(12) United States Patent
Hazart et al.

(10) Patent No.: US 10,359,994 B2
(45) Date of Patent: Jul. 23, 2019

(54) COMPUTER SYSTEM FOR PROCESSING HETEROGENEOUS MEASUREMENTS FROM VARIOUS METROLOGY APPARATUSES WITH A VIEW TO ESTIMATING VALUES OF FEATURES OF MICROELECTRONIC DEVICES, CORRESPONDING METHOD AND COMPUTER PROGRAM

(71) Applicant: COMMISSARIAT A L'ENERGIE ATOMIQUE ET AUX ENERGIES ALTERNATIVES, Paris (FR)

(72) Inventors: Jerome Hazart, Eybens (FR); Johann Foucher, Voreppe (FR)

(73) Assignee: Commissariat a l'energie atomique et aux energies alternatives, Paris (FR)

( * ) Notice: Subject to any disclaimer, the term of this patent is extended or adjusted under 35 U.S.C. 154(b) by 505 days.

(21) Appl. No.: 15/033,689

(22) PCT Filed: Nov. 3, 2014

(86) PCT No.: PCT/FR2014/052784
§ 371 (c)(1),
(2) Date: May 2, 2016

(87) PCT Pub. No.: WO2015/067879
PCT Pub. Date: May 14, 2015

(65) Prior Publication Data
US 2016/0291933 A1 Oct. 6, 2016

(30) Foreign Application Priority Data
Nov. 7, 2013 (FR) ..................................... 13 60894

(51) Int. Cl.
*G06F 7/00* (2006.01)
*G01B 21/00* (2006.01)
(Continued)

(52) U.S. Cl.
CPC ............... *G06F 7/00* (2013.01); *G01B 21/00* (2013.01); *G01N 21/47* (2013.01); *G01N 21/9501* (2013.01); *G03F 7/70625* (2013.01)

(58) Field of Classification Search
CPC .................................. G06F 7/00; G01B 21/00
See application file for complete search history.

(56) References Cited

U.S. PATENT DOCUMENTS

2006/0269130 A1\* 11/2006 Maroy ................... A61B 6/508
382/173
2012/0123748 A1\* 5/2012 Aben .................. G03F 7/70483
703/2
2013/0208973 A1 8/2013 Brill

OTHER PUBLICATIONS

Alok Vaid, et al., "A Holistic Metrology Approach: Hybrid Metrology Utilizing Scatterometry, CD-AFM and CD-SEM," Metrology, Inspection, and Process Control for Microlithography XXV, Proc. of SPIE, vol. 7971, No. 1, XP060009287, Mar. 17, 2011, (20 pages).

(Continued)

*Primary Examiner* — Marc Anthony Armand
(74) *Attorney, Agent, or Firm* — Oblon, McClelland, Maier & Neustadt, L.L.P.

(57) ABSTRACT

A computer system processing heterogeneous measurements from various metrology apparatuses includes a processor, a storage, and a software platform. The storage includes a recording of direct models expressing the heterogeneous measurements as a function of predefined features of electronic devices or parameters for processing the measurements. The software platform includes a functional cost calculation module and an interface selecting one of plural cost functions. The functional module provides an estimation of a cost by comparison of the heterogeneous measurements with an estimation of the measurements obtained by an application of the direct models to values of predefined features or processing parameters. The software platform (Continued)

Figure 1:
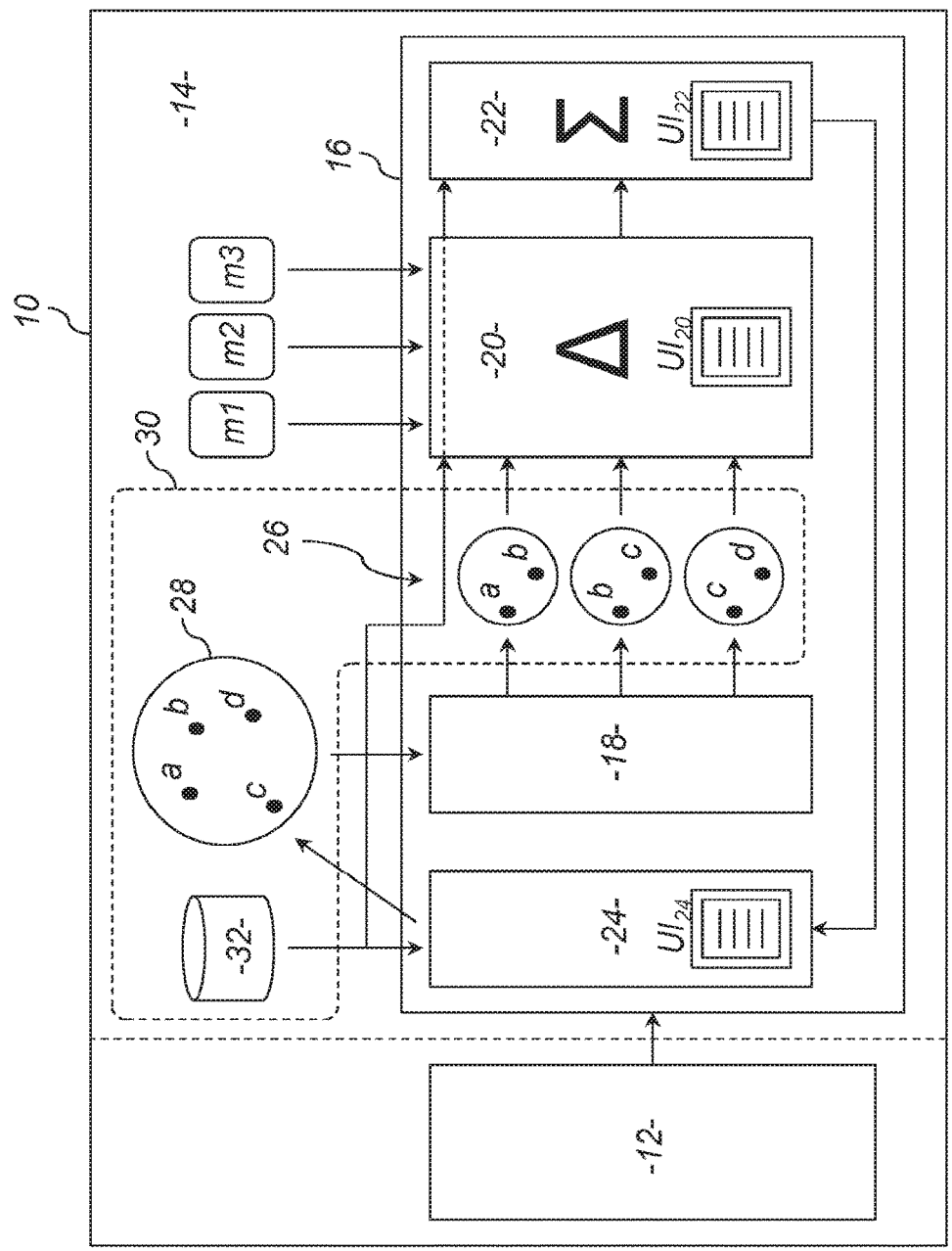

includes a functional solver module and an interface selecting one of plural solvers, for an iterative optimization by the solver of the values based on the output of the cost calculation module and by inversion of the direct models.

10 Claims, 2 Drawing Sheets

(51) Int. Cl.
    *G01N 21/47*     (2006.01)
    *G01N 21/95*     (2006.01)
    *G03F 7/20*     (2006.01)

(56) References Cited

OTHER PUBLICATIONS

International Search Report dated Apr. 7, 2015 in PCT/FR2014/052784 filed Nov. 3, 2014.
French Search Report dated Sep. 8, 2014 in FR 1360894 filed Nov. 7, 2013.

* cited by examiner

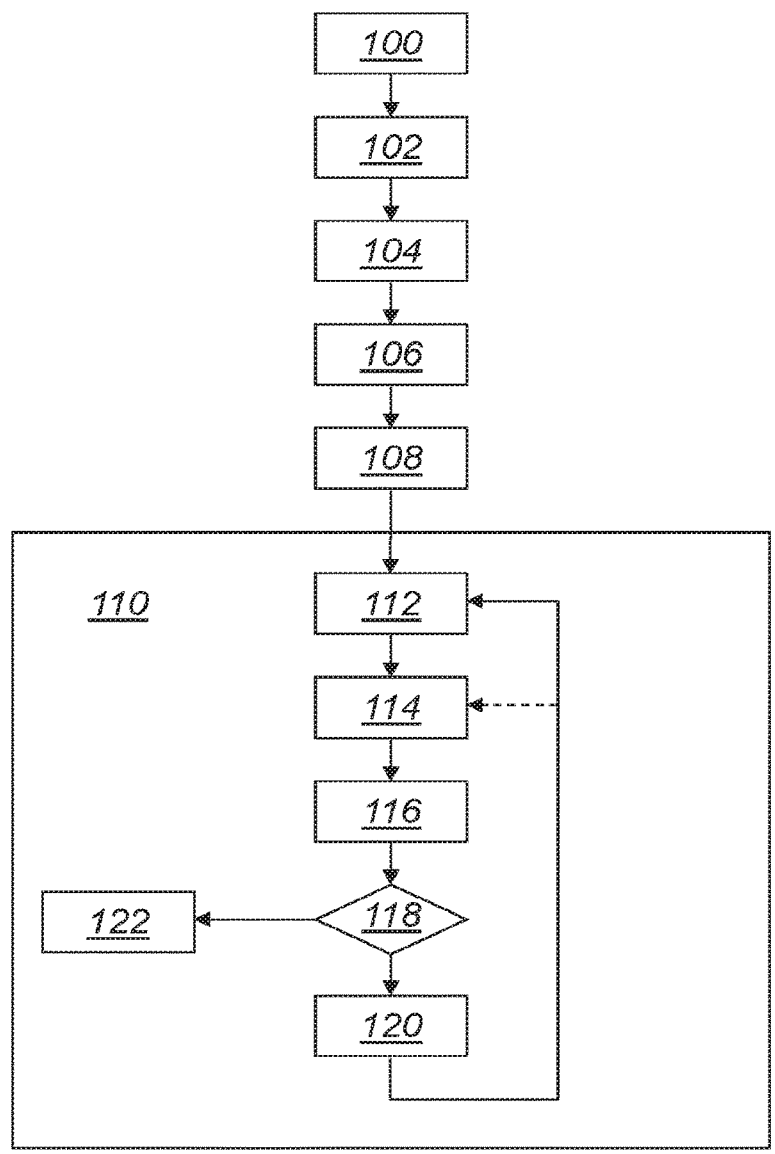

COMPUTER SYSTEM FOR PROCESSING HETEROGENEOUS MEASUREMENTS FROM VARIOUS METROLOGY APPARATUSES WITH A VIEW TO ESTIMATING VALUES OF FEATURES OF MICROELECTRONIC DEVICES, CORRESPONDING METHOD AND COMPUTER PROGRAM

This invention relates to a computer system for processing heterogeneous measurements from various metrology apparatuses with a view to estimating values of features of microelectronic devices. It also relates to a corresponding method and computer program.

Microelectronic devices today have patterns with increasingly small characteristic dimensions, and these dimensions are increasingly difficult to estimate by means of measurement equipment, called metrology apparatuses, which are used at their accuracy limit and which are highly heterogeneous in terms of the technologies used.

For example, when measuring the width of some nanometers of a pattern such as a groove or a tab formed by foundry in a microelectronic device, various measurement apparatuses having variable accuracies and speeds may generally be used:
- a scanning electron microscope provides a quick but imprecise image of the device,
- an atomic force microscope provides an image of the device less quickly but more precisely,
- optical technology, for example, an apparatus for measurement by scatterometry, ellipsometry, reflectometry, spectroscopy or the like, provides a precise spectrum quickly, but the analysis of which is complex.

There are also computer systems capable of processing raw measurement data provided by these apparatuses for providing, as precisely as possible, values for estimating features to be measured. It is therefore known to model the operation of a given apparatus for a type of pattern to be characterized, such a model defining the calculation giving the expected measurement for a given value of the feature observed, and to deduce therefrom an estimation of said feature by inversion of the model by means of a measurement actually performed. This analytical processing of measurements performed by model inversion makes it possible to compensate for the effects of the use of an apparatus at its accuracy limit. This is, for example, the case in scatterometry. In other cases, there is no actual model of the apparatus associated with the structure to be measured, but a measurement processing algorithm is defined in part by processing parameters that are to be determined with a view to then optimizing the determination of the features of the structure (for example, a level of thresholding of images obtained by electron microscopy used for analysis of the contours of an image). The model is defined in these other cases by the values of the processing parameters, which will be compared with an a priori knowledge of their probable values.

It nevertheless remains that various types of metrology apparatuses used for the same microelectronic device provide heterogeneous measurements that are difficult to process in order to obtain, in the end, a good estimation of certain features of said microelectronic device to be evaluated.

It may thus be desired to provide a computer system for processing heterogeneous measurements from various metrology apparatuses with a view to estimating values of predefined features of microelectronic devices enabling at least some of the aforementioned problems and constraints to be overcome.

A computer system is therefore proposed for processing heterogeneous measurements from various metrology apparatuses with a view to estimating values of predefined features of microelectronic devices, comprising a processor, storage means and a software platform consisting of a plurality of functional modules stored in the storage means and capable of being executed by the processor, wherein:
- the storage means comprise a space for modeling the predefined features or measurement processing parameters by recording direct models, each direct model expressing at least some of the heterogeneous measurements as a function of at least some of the predefined features or processing parameters and modeling parameters,
- the software platform comprises a functional module for calculating cost and a first associated interface dedicated to the selection of a cost function among a plurality of predefined cost functions, said functional cost calculation module providing, at the output, the estimation of a cost by comparison of the heterogeneous measurements with an estimation of said measurements obtained by means of an application of the direct models to values of the predefined features or processing parameters,
- the software platform comprises a functional solver module and a second associated interface dedicated to the selection of a solver among a plurality of predefined solvers, for iterative optimization by the solver of said values of the predefined features or processing parameters based on the output of the functional cost calculation module and by inversion of the direct models.

Thus, by providing a software platform capable of integrating a plurality of selectable cost functions and a plurality of selectable solvers, for the same global modeling of the features or parameters to be estimated by means of heterogeneous measurements, the proposed computer system makes it possible to process a wide variety of measurements from metrology apparatuses of various types by providing flexibility in the inversion. It also makes it possible to take advantage of said global modeling in order to obtain estimated values having a higher accuracy than what might be obtained individually with all of the available metrology apparatuses.

Optionally:
- the software platform also comprises a functional comparator module and a third associated interface dedicated to the selection of a comparator among a plurality of predefined comparators, said functional comparator module providing, at the output, the comparison of the heterogeneous measurements with the estimation of said measurements obtained by means of the application of the direct models to the values of predefined features or processing parameters, and
- the functional cost calculation module is designed to provide the estimation of the cost based on the output of the functional comparator module.

Also optionally:
- the modeling space comprises the recording of a direct meta-model expressing all of the heterogeneous measurements as a function of all of the predefined features or processing parameters and meta-modeling parameters, and the software platform comprises a functional module for demultiplexing the meta-model in order to obtain said direct models.

Also optionally, each direct model is associated exclusively with a single type of metrology apparatus.

Also optionally, constraints linking certain of the predefined features or processing parameters with one another are recorded in the storage means and are intended to be taken into account by the functional cost calculation module or by the functional solver module for optimization of said values of predefined features or processing parameters.

Also optionally, a plurality of cost functions are recorded in the storage means, including:
- a distance sum function, for example using L1 norm,
- an entropic function for kernel probability density estimation,
- a Huber loss type function,
- a bisquare cost function, and
- a Hampel cost type function.

Also optionally, a plurality of solvers are recorded in the storage means, including:
- a solver for solving systems of algebraic equations with at least one unknown,
- a genetic algorithm solution solver,
- a simulated annealing solution solver,
- a local nonlinear optimization solver without constraints, and
- a local nonlinear optimization solver with constraints.

Also optionally, the direct models are defined in order to express heterogeneous measurements from various types of metrology apparatuses, including:
- measurements from a scanning or transmission electron microscope,
- measurements from an atomic force microscope,
- measurements obtained by scatterometry, ellipsometry, reflectometry or spectroscopy,
- reflectivity or diffraction X-ray measurements, and
- measurements from an optical microscope.

A method is also proposed for estimating values of predefined features of microelectronic devices on the basis of heterogeneous measurements from various metrology apparatuses, comprising the following steps:
- modeling the predefined features or parameters for processing the measurements by recording direct models in storage means, each direct model expressing at least some of the heterogeneous measurements as a function of at least some of the predefined features or processing parameters and modeling parameters,
- receiving the heterogeneous measurements, by a software platform executed by a processor having access to the storage means,
- selecting, by means of a first dedicated interface of the software platform, a cost function among a plurality of predefined cost functions,
- selecting, by means of a second dedicated interface of the software platform, a solver among a plurality of predefined solvers, and
- iterative optimization of values of the predefined features or processing parameters, by:
  - estimating, by the processor and by means of the cost function selected, a cost by comparison of the heterogeneous measurements with an estimation of said measurements obtained by means of an application of the direct models to said values of predefined features or processing parameters,
  - updating, by the processor and by means of the selected solver, said values of predefined features or processing parameters on the basis of the estimated cost and by inversion of the direct models.

Finally, a computer program downloadable from a communication network and/or recorded on a computer-readable medium and/or capable of being executed by a processor is also proposed, including instructions for executing steps of a method for estimating values of predefined features of microelectronic devices according to the invention, when said program is executed on a computer.

The invention will be easier to understand in view of the following description, provided solely as an example and with reference to the appended drawings, wherein:

FIG. 1 schematically shows the general structure of a computer system for processing heterogeneous measurements from various metrology apparatuses with a view to estimating values of predefined features of microelectronic devices, according to an embodiment of the invention, FIG. 2 shows the successive steps of a method for estimating values of predefined features of microelectronic devices implemented by the computer system of FIG. 1.

The computer system 10 shown in FIG. 1, for example a computer, comprises a processor 12 conventionally associated with storage means 14, for example a RAM memory, for storing data files and computer programs capable of being executed by the processor 12.

Among the computer programs capable of being executed by the processor 12, a software platform 16 consisting of a plurality of functional modules 18, 20, 22, 24 is stored in the memory 14. The computer system 10 as shown in FIG. 1 thus functionally comprises four computer programs represented by the functional modules 18, 20, 22, 24, or four functions of the same computer program as represented by the software platform 16. It should also be noted that the functional modules 18, 20, 22, 24 are presented as being distinct, but this distinction is purely functional. They may also be grouped according to all possible combinations in one or more software programs. Their functions may also be at least partially micro-programmed or micro-wired in dedicated integrated circuits. Thus, alternatively, the computer system 10 may take the form of an electronic device comprised at least partially of digital circuits (without a computer program) for carrying out the same actions.

The computer system 10 is designed for processing heterogeneous measurements from various metrology apparatuses with a view to estimating values of predefined features of microelectronic devices, said estimation possibly being made by means of an optimization of measurement processing parameters. In the non-limiting example shown in FIG. 1, three heterogeneous measurements m1, m2 and m3 are stored in the memory 14, and four predefined features of microelectronic devices or measurement processing parameters denoted a, b, c and d are to be estimated. Measurement m1 is, for example, provided by a scanning electron microscope, measurement m2 is provided by an atomic force microscope and measurement m3 is provided by a scatterometry apparatus. Each of these measurements may come from other metrology apparatuses such as a transmission electron microscope, a reflectivity diffraction or X-ray measurement apparatus, an optical microscope, and so on. Measurements m1, m2 and m3 may be mono- or multi-value data. The features or parameters a, b, c and d, expressing, for example, characteristic dimensions of integrated circuit patterns or measurement processing parameters to be determined, are stored in the form of direct models 26 or a direct meta-model 28, of which they constitute the variables, in a modeling space 30, itself also stored in the memory 14. Each model of the set of direct models 26 mathematically expresses at least some of the heterogeneous measurements m1, m2, m3 as a function of at least some of the features or parameters a, b, c, d and modeling parameters. This mathematical expression of measurements m1, m2, m3 as a function of the features or parameters a, b, c, d may be performed concretely, for example, by means of systems of equations, probabilistic functions or random drawings. The optional meta-model 28 represents the sum or union of said models. Finally, some of the features or parameters a, b, c and d may be linked with one another by constraints 32 also stored in the memory 14 in the modeling space 30.

More specifically, in a preferred embodiment of the invention, the direct meta-model 28 mathematically expresses all of the heterogeneous measurements m1, m2, m3 as a function of all of the predefined features or parameters a, b, c, d and meta-modeling parameters. The modeling space 30 including said meta-model 28 may then be considered from the perspective of the computer implementation as a vector space, the dimensions of which correspond to variables a, b, c and d of the meta-model 28.

The constraints 32, linking certain of said variables with one another or concerning certain variables in isolation, may reduce the number of dimensions of the vector space. A constraint may, for example, impose a value, or a range of values, on a variable. Another constraint may, for example, impose a relation, of equality or inequality, linear or not, between a number of said variables. The constraints may also be expressed by means of cost functions not linked to the measurements. There may thus be cost functions associating a value to be minimized with certain variables of the meta-model 28. For example, if it is sought to express the fact that variables a and b are almost equal, they may be associated with a cost function based on the squared absolute value of their difference. It should be noted that such a cost function may produce a loss model coupling (if the variables coupled by the cost function belong to different models), the solution of which is known to a person skilled in the art.

In this same preferred embodiment shown in FIG. 1, the functional module 18 of the software platform 16 is a demultiplexing module of the meta-model 28 for obtaining direct models 26, each direct model being associated exclusively with a single type of metrology apparatus, i.e. a single measurement among the three heterogeneous measurements m1, m2 and m3. A first direct model, in which the variables are the predefined features or parameters a and b is thus, for example, associated with the measurement m1 obtained from the scanning electron microscope by means of a mathematical function $f_1$ such that $m1=f_1(a,b,p_1)$ where $p_1$ designates a set of parameters of this direct model. A second direct model in which the variables are the predefined features or parameters b and c is associated with the measurement m2 obtained from the atomic force microscope by means of a mathematical function $f_2$ such that $m2=f_2(b,c,p_2)$ where $p_2$ designates a set of parameters of this direct model. Finally, a third direct model in which the variables are the predefined features or parameters c and d is associated with measurement m3 obtained from the scatterometry apparatus by means of a mathematical function $f_3$ such that $m3=f_3(c,d,p_3)$ where $p_3$ designates a set of parameters of this direct model. The three above-mentioned direct models may be considered to be vector sub-spaces of the modeling space 30, extracted by means of the demultiplexing module 18.

From the perspective of the computer implementation, the measurement data m1, m2 and m3 are encapsulated in objects. Observables are created in order to make the link between said objects and the aforementioned direct models. These observables take the form of the aforementioned mathematical functions. They consist in selecting the variables of the direct models with which they are associated among all of the variables of the modeling space; selecting the measurements associated with them; applying the relations defined by the associated functions between the variables and the measurements.

The functional module 20 of the software platform 16 is a comparator module associated with an interface $UI_{20}$ dedicated to the selection of one comparator among a plurality of predefined comparators. The predefined comparators are, for example, functions of point-to-point distances or pseudo-distances defined according to a plurality of norms or other possible functions. By "pseudo-distance", we mean a function that returns a higher weight when the data to be compared are "distant", but that does not necessarily have all of the properties of a distance function. Other comparison functions may be freely defined and added by a user of the computer system 10 to the list of selectable comparators. Whatever, the selected comparator is, the comparator module 20 receives, at the input, the heterogeneous measurements m1, m2, m3 as well as an estimation of said measurements obtained by means of the application of the aforementioned direct models to current values of predefined features or parameters a, b, c, d. It provides, at the output, a point-to-point comparison of the measurements m1, m2, m3 with their respective estimations. If a portion of the constraints 32 is expressed by means of at least one cost function between certain of variables a, b, c, d, the comparator module 20 also compares the variables concerned with one another.

The functional module 22 of the software platform 16 is a cost calculation module associated with an interface $UI_{22}$ dedicated to the selection of a cost function among a plurality of predefined cost functions. The predefined cost functions are, for example, sums of distances or pseudo-distances defined according to a plurality of norms (in particular norm L1, which makes it possible to define a robust cost function) or other possible functions. Another example of a cost function is an entropic function for performing a kernel probability density estimation. Other cost functions may be freely defined and added by a user of the computer system 10 to the list of selectable cost functions. In particular, other robust cost functions such as the Huber loss function, a bisquare cost function or the Hampel cost function may be defined. Regardless of the cost function selected, the cost calculation module 22 receives, at the input, the output of the comparator module 20. It provides, at the output, an estimation of a cost. If a portion of the constraints 32 is expressed by means of at least one cost function between certain of variables a, b, c, d, the cost calculation module 22 also integrates this cost function in addition to the predefined selectable cost function.

A distinction has been made between the comparator module 20 and the cost calculation module 22, but, alternatively, a single undifferentiated cost calculation module may perform the two above-mentioned functions.

The functional module 24 of the software platform 16 is a solver module associated with an interface $UI_{24}$ dedicated to the selection of a solver among a plurality of predefined solvers. The predefined solvers are, for example, solvers for solutions of algebraic equation systems with at least one unknown, genetic algorithm solution solvers, simulated annealing solution solvers, local nonlinear optimization solvers without constraints (for example, Levenberg-Marquardt, Simplex, Newton, quasi-Newton or "Trust-region"), local nonlinear optimization solvers with constraints (for example, "Active set", "Sequential Quadratic Programming", "Trust-region" or "Interior point"), and so on. Other solvers may be freely defined and added by a user of the computer system 10 to the list of selectable solvers. Regardless of the solver selected, the solver module 24 receives, at the input, the output of the cost calculation module 22 as well as the constraints 32 other than those expressed by means of cost functions. By means of these constraints 32 and by inversion of the direct meta-model 28 (which amounts to inverting all of the direct models 26), it provides, at the output, an updating of the current values of the predefined features or parameter a, b, c and d, for an interactive optimization of said values. It may thus comprise a tester capable of applying a stop criterion (number of iterations exceeding a certain limit, variations of the updated values below a certain threshold, cost provided at the output of the functional module 22 below a certain threshold, and so on) in a successive execution loop of the functional modules 18, 20, 22 and 24, for providing definitive values of these predefined features or processing parameters. Alternatively, if it is the cost value provided by the functional module 22 that is tested, the tester may be arranged functionally between the modules 22 and 24.

The operation of the computer system 10 will now be described with reference to FIG. 2, with the implementation of a method for estimating predefined features of microelectronic devices or parameters for processing measurements on the basis of heterogeneous measurements from various metrology apparatuses.

In an first initialization step 100, the meta-model 28 and the constraints 32 are recorded in the modeling space 30 of the memory 14.

In a step 102, the heterogeneous measurements m1, m2 and m3 are recorded in the memory 14 and provided as input parameters for the software platform 16.

In a first selection step 104, a comparator is selected from the plurality of available comparators, by means of the interface $UI_{20}$. In a second selection step 106, a cost function is selected from the plurality of available cost functions, by means of the interface $UI_{22}$. Finally, in a third selection step 108, a solver is selected from the plurality of available solvers, by means of the interface $UI_{24}$.

It should be noted that the order in which steps 100 to 108 may be executed is unimportant. Once executed, these steps are followed by a loop 110 of steps, which will now be described.

In a first step 112 of said loop of steps, performed by executing the demultiplexing module 18, the direct models 26 are obtained from the meta-model 28 with current values of the predefined features or parameters a, b, c and d (values initialized in the first iteration of the loop of steps 110).

In a second step 114 of said loop of steps, performed by executing the comparator module 20, the measurements m1, m2 and m3 are compared with the estimations of said measurements obtained by applying the direct models 26 to the current values of the predefined features or parameters a, b, c and d. If a portion of the constraints 32 is expressed by means of at least one cost function between certain of variables a, b, c, d, the variables concerned are also compared with one another.

In a third step 116 of said loop of steps, performed by executing the cost calculation module 22, a cost is calculated on the basis of the output of the functional comparator module 20. If a portion of the constraints 32 is expressed by means of a cost function between certain of variables a, b, c, d, the cost calculated in said step takes it into account.

In a possible embodiment of the invention, in which the cost value is tested in order leave the loop of steps 110 or not, the third step 116 is followed by a test step 118 during which the cost is compared to a predetermined threshold.

If the cost exceeds this threshold, the method goes to a step 120 of executing the solver module 24 in order to update the current values of the predefined features or parameters a, b, c and d. Step 120 is followed by a return to step 112, or optionally directly to step 114 if it is not necessary to carry out the demultiplexing of the direct meta-model 28 multiple times.

Otherwise, the method goes to a step 122 of leaving the loop of steps 110 and ending the iterative optimization of values of the predefined features or processing parameters.

It clearly appears that a computer system as described above makes it possible to process a wide variety of measurements from various metrology apparatuses by providing flexibility in the inversion of a set of models owing to the possible selection of a comparator, a cost function and a solver among a plurality of comparators, cost functions and solvers made available by the software platform. It also makes it possible to take advantage of this global modeling in order to obtain estimated values having a higher accuracy than what might be obtained individually for all available metrology apparatuses.

It should also be noted that the invention is not limited to the embodiment described above. It will indeed appear to a person skilled in the art that various modifications may be made to the embodiment described above, in light of the teaching which has just been disclosed. In the claims below, the terms used must not be interpreted as limiting the claims to the embodiment disclosed in the present description, but must be interpreted so as to include all of the equivalents that the claims are intended to cover in view of their wording, and which are within the abilities of a person skilled in the art applying general knowledge to the implementation of the teaching which has just been disclosed.

The invention claimed is:

1. A computer system for processing heterogeneous measurements from metrology apparatuses to estimate values of predefined features of microelectronic devices, comprising:
    a processor;
    a storage; and
    a software platform including a plurality of functional modules stored in the storage and configured to be executed by the processor;
    wherein the storage comprises a space for modeling the predefined features or measurement processing parameters by recording direct models, each direct model expressing at least some of the heterogeneous measurements as a function of at least some of the predefined features or processing parameters and modeling parameters;
    wherein the software platform comprises a functional module for calculating cost and a first associated interface dedicated to selection of a cost function among a plurality of predefined cost functions, the functional cost calculation module providing, at an output, an estimation of a cost by comparison of the heterogeneous measurements with an estimation of the measurements obtained by an application of the direct models to values of the predefined features or processing parameters;
    wherein the software platform comprises a functional solver module and a second associated interface dedicated to selection of a solver among a plurality of predefined solvers, for iterative optimization by the solver of the values of the predefined features or processing parameters based on the output of the functional cost calculation module and by inversion of the direct models.

2. A computer system according to claim 1, wherein:
the software platform further comprises a functional comparator module and a third associated interface dedicated to selection of a comparator among a plurality of predefined comparators, the functional comparator module providing, at an output, a comparison of the heterogeneous measurements with the estimation of the measurements obtained by the application of the direct models to the values of predefined features or processing parameters; and
the functional cost calculation module is configured to provide the estimation of the cost based on the output of the functional comparator module.

3. A computer system according to claim 1, wherein:
the modeling space comprises recording of a direct meta-model expressing all of the heterogeneous measurements, each being measured by a respective one of different metrology apparatuses, as a function of all of the predefined features or processing parameters and meta-modeling parameters, and
the software platform comprises a functional module for demultiplexing the meta-model to obtain the direct models.

4. A computer system according to claim 3, wherein each direct model is associated exclusively with a single type of metrology apparatus.

5. A computer system according to claim 1, wherein constraints linking certain of the predefined features or processing parameters with one another are recorded in the storage and can be taken into account by the functional cost calculation module or by the functional solver module for optimization of the values of predefined features or processing parameters.

6. A computer system according to claim 1, wherein a plurality of cost functions are recorded in the storage, including:
a distance sum function,
an entropic function for kernel probability density estimation,
a Huber loss type function,
a bisquare cost function, and
a Hampel cost type function.

7. A computer system according to claim 1, wherein a plurality of solvers are recorded in the storage, including:
a solver for solving systems of algebraic equations with at least one unknown,
a genetic algorithm solution solver,
a simulated annealing solution solver,
a local nonlinear optimization solver without constraints, and
a local nonlinear optimization solver with constraints.

8. A computer system according to claim 1, wherein the direct models are defined for expressing heterogeneous measurements from various types of metrology apparatuses, including:
measurements from a scanning or transmission electron microscope,
measurements from an atomic force microscope,
measurements obtained by scatterometry, ellipsometry, reflectometry or spectroscopy, reflectivity or diffraction X-ray measurements, and
measurements from an optical microscope.

9. A method for estimating values of predefined features of microelectronic devices on the basis of heterogeneous measurements from various metrology apparatuses, comprising:
modeling the predefined features or parameters for processing the measurements by recording direct models in a storage, each direct model expressing at least some of the heterogeneous measurements as a function of at least some of the predefined features or processing parameters and modeling parameters;
receiving the heterogeneous measurements, by a software platform executed by a processor having access to the storage;
selecting, by a first dedicated interface of the software platform, a cost function among a plurality of predefined cost functions;
selecting, by a second dedicated interface of the software platform, a solver among a plurality of predefined solvers; and
iterative optimization of values of the predefined features or processing parameters, by:
estimating, by the processor and by the cost function selected, a cost by comparison of the heterogeneous measurements with an estimation of the measurements obtained by an application of the direct models to the values of predefined features or processing parameters,
updating, by the processor and by the selected solver, the values of predefined features or processing parameters on the basis of the estimated cost and by inversion of the direct models.

10. A non-transitory computer readable medium that stores a computer program to be executed by a computer, comprising computer executable instructions for executing a method for estimating values of predefined features of microelectronic devices on the basis of heterogeneous measurements from various metrology apparatuses, the method comprising:
modeling the predefined features or parameters for processing the measurements by recording direct models in a storage, each direct model expressing at least some of the heterogeneous measurements as a function of at least some of the predefined features or processing parameters and modeling parameters;
receiving the heterogeneous measurements, by a software platform executed by a processor having access to the storage;
selecting, by a first dedicated interface of the software platform, a cost function among a plurality of predefined cost functions;
selecting, by a second dedicated interface of the software platform, a solver among a plurality of predefined solvers; and
iterative optimization of values of the predefined features or processing parameters, by:
estimating, by the processor and by the cost function selected, a cost by comparison of the heterogeneous measurements with an estimation of the measurements obtained by an application of the direct models to the values of predefined features or processing parameters,
updating, by the processor and by the selected solver, the values of predefined features or processing parameters on the basis of the estimated cost and by inversion of the direct models.

* * * * *